United States Patent
Ding et al.

(10) Patent No.: US 11,765,997 B2
(45) Date of Patent: Sep. 26, 2023

(54) **METHOD FOR IMPROVING NUTRIENT SUPPLY OF FEMALE FLORAL BRANCHES OF *POPULUS DELTOIDES* ARTIFICIAL HYBRIDIZATION**

(71) Applicant: Research Institute of Forestry Chinese Academy of Forestry, Beijing (CN)

(72) Inventors: Changjun Ding, Beijing (CN); Yufeng Dong, Beijing (CN); Weixi Zhang, Beijing (CN); Xiaohua Su, Beijing (CN); Shanwen Li, Beijing (CN); Yanping Wang, Beijing (CN); Qinjun Huang, Beijing (CN); Lei Wang, Beijing (CN)

(73) Assignee: Research Institute of Forestry Chinese Academy of Forestry, Beijing (CN)

( * ) Notice: Subject to any disclaimer, the term of this patent is extended or adjusted under 35 U.S.C. 154(b) by 0 days.

(21) Appl. No.: 17/584,408

(22) Filed: Jan. 26, 2022

(65) Prior Publication Data

US 2022/0248611 A1 Aug. 11, 2022

(30) Foreign Application Priority Data

Feb. 4, 2021 (CN) .......................... 202110166641.4

(51) Int. Cl.
*A01H 1/02* (2006.01)
*A01G 2/35* (2018.01)
*A01G 31/00* (2018.01)

(52) U.S. Cl.
CPC ................ *A01G 2/35* (2018.02); *A01G 31/00* (2013.01); *A01H 1/02* (2013.01)

(58) Field of Classification Search
CPC ............. A01G 2/35; A01G 31/00; A01H 1/02
See application file for complete search history.

(56) References Cited

PUBLICATIONS

Peng et al. Flora, 208:479-487 (Year: 2013).*
Ahmadloo et al. Journal of Forest Science, 64(5):207-215 (Year: 2018).*
Jackson et al. NDSU Extension Service, pp. 1-7 (Year: 1998).*

* cited by examiner

*Primary Examiner* — Keith O. Robinson

(57) ABSTRACT

The application provides a method for improving nutrient supply of female floral branches of *Populus deltoides* artificial hybridization. According to the technical links of the hybridization operation, the method separately integrates and improves the cultivation of female floral branch nutrient-supply seedlings (i.e., grafting rootstocks of floral branches), the pre-management of female floral branch nutrient-supply seedlings, the hydroponic management of floral branches, the Marching between female floral branches and rootstocks, the management of female floral branch nutrient-supply seedlings and the hydroponic management of female floral branches, so the goal of improving the seed-setting rate and quality of poplar hybrid seeds which came from the floral branches cultured in water has been achieved. Compared with the conventional method, the method of the invention not only can realize good seed quality, but also improve the seed-setting rate, and has a remarkable effect when applied to *Populus deltoides* artificial hybridization.

2 Claims, No Drawings

METHOD FOR IMPROVING NUTRIENT SUPPLY OF FEMALE FLORAL BRANCHES OF *POPULUS DELTOIDES* ARTIFICIAL HYBRIDIZATION

TECHNICAL FIELD

The invention belongs to the technical field of forest hybridization, and relates to a method for improving nutrient supply of female floral branches of *Populus deltoides* artificial hybridization, and in particular to a method for improving the nutrient supply of female floral branches to increase the seed-setting rate and quality of poplar hybrid seeds which came from the floral branches cultured in water.

BACKGROUND

Poplar hybridization is the most important method for poplar improvement. Most cultivars at home and abroad are selected through this method, because hybrids have excellent quality and adaptability required. In addition to a small number of natural hybrids in nature, artificial hybridization is the most important way to obtain hybrid variety. According to the environment in which the female parent of the seed develops, artificial hybridization can be divided into the following two types: one is the artificial hybridization on the outdoor tree, and the other is the indoor artificial hybridization after the female parent's floral branches are cut. Indoor artificial hybridization can avoid some difficulties in the operation of hybridization on large trees in the wild, solve the problem of inconsistency between the flowering period and production area of the parents, and facilitate to regulate the operation and environmental conditions during the entire process of hybridization and sowing. The indoor artificial hybridization methods reported mainly include cutting branch-hydroponics, soil culture method after cutting branch-hydroponics, floral branch grafting method, etc, wherein poplar hybrid seeds which came from the floral branches cultured in water is currently one of the important and effective breeding methods for obtaining new poplar varieties, and is also the method that is commonly used in indoor hybridization at home and abroad. However, in the process of cutting branch-hydroponics of female floral branches, microbial infection and excessive mucus secretion appear at the base of the cutting branches, which can easily cause root rot and hypoxia and affect root formation, thus affecting the absorption and transportation of water and some nutrients, and hindering flower development and seed maturation. Moreover, a lot of manpower and time is necessary during the hydroponics hybridization, and the base of cutting branches is often needed to be cleaned and pruned; oxygen injection and water change of flower branches, etc. are also necessary; meanwhile, the nutrients required for flower development and seed maturation almost completely depend on the nutrients stored in the floral branches, so unwanted inflorescences must be removed from the floral branches to allow a small amount of reserved branches and seeds to develop. *Populus deltoides*, which is famous for fast growth, needs a long time to produce roots, and it takes a long time for seeds to mature. In hydroponic hybridization, inflorescences are easy to fall off. Even if seeds are obtained, the breeding efficiency is very low because the quantity is small and the seeds are immature. In order to solve the problems during the cutting branch-hydroponics hybridization, some solutions have been reported. Soil culture method after cutting branch-hydroponics is to add nutrient soil after the adventitious roots occur in the hydroponics, which can reduce the pruning, oxygen injection and water change of the hydroponics. Meanwhile, floral branches absorb nutrients from the soil, which is beneficial to embryo development, but it is easy to damage the fibrous roots during operation, and it is also easy to affect the development of embryos and seeds after fertilization during the conversion process from hydroponics to soil culture; especially, the application of tree species that take root late and hard to take root is limited. The traditional grafting method is to breed the rootstock first, and then to graft the female floral branches to the rootstock by Marching method. The floral branches can gradually use the root system of the rootstock to obtain more nutrients from the soil, so as to solve the problems of artificial hybridization such as late rooting and long seed maturity of *Populus deltoides*. However, because the the specific operation technical data are inaccurate, the embryo and seed development process may be directly affected by the grafting effect, and only few inflorescences can be retained. Therefore, how to further improve the seed-setting rate and quality of *Populus deltoides* hybrid seeds in the early stage of hybridization technology is the technical bottleneck that needs to be solved urgently in the current *Populus deltoides* hybrid seeds which came from the floral branches cultured in water.

SUMMARY

In order to further improve the seed-setting rate and quality of poplar hybrid seeds which came from the floral branches cultured in water, the invention improves and upgrades the previous technology to provide a method for improving the nutrient supply of the female floral branches of lack poplar artificial hybridization.

In order to achieve the above objective, the invention is specifically achieved through the following technical solutions:

A method for improving the nutrient supply of the female floral branches of *Populus deltoides* artificial hybridization, including the following steps:

(1) cultivation of female floral branch nutrient-supply seedlings, i.e. floral branch grafting rootstocks in March of the year before cross pollination, the branches of the same year of the hybrid female parent with the same pedigree number are selected to make cuttings, and then cuttage propagation is performed; after all the seedlings have fallen leaves at the end of November, the weakly lignified part of the upper part is cut off, keeping the seedling height of 1.5-2.0 m, and then the seedling container is moved from the field to the greenhouse;

or for 1-year-old cuttings that are not easy to obtain female floral branch strain, *Populus deltoides* or *P. euramerican* with the same genetic relationship or close genetic distance with the female branch strain is selected for cuttage or the current year seedlings are transplanted in the autumn of 1 year before the floral branch is picked, and transplanting is completed before the seedlings fall leaves; after transplanting, the weakly lignified part of the upper part of the seedlings is truncated, and the number of transplanted seedlings is 2-3 times the number of hydroponic floral branches, so as to select seedlings with similar thickness of floral branches as rootstocks for grafting;

(2) the management of female floral branch nutrient-supply seedlings, i.e. floral branch grafting rootstocks 10-15 days before the hydroponics of cross-pollination floral branch, the nutrient-supply seedlings are placed in a room with a room temperature of 20° C. and a relative humidity of 50-60%, and gibberellin solution with a concentration of 10-50 mg/L is sprayed on the upper part of the seedling every 5-7 days until the seedlings are wet, and spraying is stopped after the leaf buds germinate; watering with flowerpots, the nutrient solution is poured on the poplar rootstock growth substrate in the pot, and the nutrient solution is composed of 0.02-0.05% of borax, 0.1-0.2% of superphosphate and 0.05-0.1% of compound urea aqueous solution;

(3) hydroponic management of male and female floral branches after the leaf buds of the nutrient-supply seedlings start to germinate for 2-3 days, the hydroponics of the male floral branches is started; after 5-7 days of the hydroponics of the male floral branches, the hydroponics of the hybrid female floral branches is started, keeping the room temperature at about 20° C. and the relative humidity of 50-60% during hydroponics;

4) the grafting of hydroponic female floral branches and nutrient-supply seedlings, i.e. Marching rootstocks the female flower branches are hydroponically cultured indoors at room temperature of about 20° C. and relative humidity of 50-60%; the female floral branches and the nutrient-supply seedlings are grafted, and the grafting method is Marching method;

(5) after grafting, the management of the nutrient supply of the female floral branches, i.e. Marching rootstocks watering is carried out timely according to the moisture status of nutrient-supply seedling substrate every 5-7 days, and nutrient solution is applied at the same time when watering; the nutrient solution consists of 0.02-0.05% of borax, 0.1-0.2% of superphosphate and 0.05-0.1% of compound urea aqueous solution; the substrate temperature for rootstock growth is kept at 20-22° C. to facilitate the rapid absorption of substrate nutrients by the rootstock roots;

(6) hydroponic management of female floral branches after Marching is completed the grafted female floral branches are then placed in a hydroponic container for hydroponics; the initial indoor temperature is kept at about 20° C. during the day and no less than 5° C. at night, and the water is changed every 2-3 days;

when the temperature rises in the later stage, the water is changed every 1-2 days, and the nutrient solution is added when changing the water; the nutrient solution is composed of 0.02-0.05% of borax, 0.1-0.2% of superphosphate and 0.05-0.1% of compound urea aqueous solution; the nutrient solution is sprayed on the back of the leaves of the female floral branches.

Furthermore, a soil ball is necessary when transplanting in step (1), and the diameter of the soil ball is slightly smaller than the inner diameter of the container to be transplanted, and the height of the soil ball is 6-10 cm lower than the container; the bottom and surroundings of the container are filled with turf and soil mixed in a volume ratio of 2:1, and after compaction, the roots are irrigated with a mixed solution of 100-150 mg/L of indoleacetic acid and naphthylacetic acid when watering, so as to facilitate the timely restoration of root growth. The container adopts a portable plastic container or a non-woven seedling bag.

Further, in step (3), it is better to choose a plastic container with a diameter of 25-35 cm and a depth of 40-50 cm as the container for hydroponics of female flower branches. A circular water outlet with a diameter of 1.5-2 cm is opened 0.3-0.5 cm away from the bottom of one side of the plastic container, and a cylindrical rubber plug with a length of 3-5 cm is matched with the circular water outlet.

Furthermore, the thickness of poplar seedlings used for grafting in step (4) should be similar to or slightly thinner than that of female floral branches; 1-3 poplar seedlings are grafted for each female floral branch according to its height; the grafting position should be at the bottom of the flower bud and as close as possible to the flower bud; when grafting more than 2 poplar seedlings, the grafting operation should be carried out in different positions of the female floral branches.

Further, when changing the water in step (6), the cuts of the branches are rinsed to prevent the mucus secreted from affecting water absorption; if the cuts at the lower end of the branches have changed color or even rotted, trim the cuts in time and clean the hydroponics container; oxygen is introduced into the hydroponic solution once a day to ensure that there is enough oxygen in the water.

The beneficial effects of the invention are as follows:

In order to improve the nutrient supply of the female floral branches of *Populus deltoides* artificial hybridization, thereby improving the seed-setting rate and quality of hybrid seeds, the invention improves the technology developed in the early stage by adopting the technology of cultivating nutrient-supply seedlings, optimizing grafting and feeding method, improving the continuous nutrient supply of flower branches, the goal of improving the seed-setting rate and quality of poplar hybrid seeds which came from the floral branches cultured in water has been achieved. Compared with the conventional method, the method of the invention not only can realize good seed quality, but also improve the seed-setting rate, and the method is simple and easy to operate, which can be applied to the production of poplar hybridization on a large scale.

DESCRIPTION OF THE EMBODIMENTS

The technical solutions of the invention will be clearly and completely described below in combination with specific embodiments of the invention. Obviously, the described embodiments are only a part of the embodiments of the invention, rather than all the embodiments. Based on the embodiments in the invention, all other embodiments obtained by ordinary technicians in the field without creative work are within the scope of the invention.

The embodiment below provides a method for improving the nutrient supply of female floral branches of *Populus deltoides* in artificial hybridization, so as to improve the seed-setting rate and quality of poplar hybrid seeds which came from the floral branches cultured in water, which is achieved through the following steps:

Step 1, collection of floral branches: floral branches should be collected before the sap flows. The collection time in North China is generally at the end of January and early February. The branches that grow sturdy and free from diseases and insect pests in the upper part of the crown should be collected. Male flower branches are 2-3 year-old branches with a thickness of 1.5-2.5 cm, and female flower branches are 2-3 year-old branches with a thickness of 2.5-3.5 cm.

Step 2, treatment of floral branches: the female floral branches are integrally sealed with plastic film, and placed in a refrigerator at 2-3° C. for 5-7 days. Keep female and male branches with flower buds with a length of about 120 cm respectively, remove the excessive growth of branches, and keep all flower buds after removing the diseased, weak and defective flower buds. Hang a label on each flower branch, indicating the variety, collection time and place, etc.

Step 3, cultivation of female floral branch nutrient-supply seedlings, i.e. grafting rootstocks: the name of the female floral branch strain is determined according to the hybridization plan, and in March of the year before cross pollination, the branches of the same year are selected to make cuttings, and then cuttage propagation is carried out. The inner diameter of the cuttage container is 30-40 cm, and depth is 40-50 cm; the container should be better made of tile or porcelain. The lower ⅓-½ of the cuttage container should be buried in the soil, and cuttage propagation is carried out in the container. After all the seedlings have fallen leaves at the end of November, the weakly lignified part of the upper part is cut off, keeping the seedling height of 1.5-2.0 m, and then the seedling container is moved from the field to the greenhouse.

The above series of measures are obtained through repeated experiments and comparisons, which can effectively improve the quality of seedlings, increase the survival rate of transplanting, and quickly restore the vitality of seedlings after transplanting, and finally provide effective nutrient supply for floral branches.

For 1-year-old cuttings that are not easy to obtain female floral branch strain, *Populus deltoides* or *P. euramerican* with the same or close genetic relationship with the female branch strain may be selected for cuttage or the current year seedlings are transplanted in the autumn of 1 year before the floral branch is picked, the diameter of seedlings at one meter from the ground is generally 1.5-2.5 cm; transplanting is completed before the seedlings fall leaves, usually from the end of October to the beginning of November; a soil ball is necessary when transplanting in step (1), and the diameter of the soil ball is slightly smaller than the inner diameter of the container to be transplanted, and the height of the soil ball is 6-10 cm lower than the container; the bottom and surroundings of the container are filled with turf and soil mixed in a volume ratio of 2:1, and after compaction, the roots are irrigated with a mixed solution of 100-150 mg/L of indoleacetic acid and naphthylacetic acid when watering, so as to facilitate the root system to recover and grow in time, the container is a light plastic container or a non-woven seedling bag. After transplanting, the weakly lignified part of the upper part of the seedlings is truncated, and the height of the seedlings is generally kept at 2.0-2.5 m to improve the survival rate of transplanting and to facilitate the next step of seedling transportation and grafting operations. The number of transplanted seedlings is determined according to the number of hybrid combinations to be carried out, generally 2-3 times the number of hydroponic floral branches, so as to select seedlings with similar thickness of floral branches as rootstocks for grafting;

Step 4, management of female floral branch nutrient-supply seedlings, i.e. grafting rootstocks: place the potted poplar seedlings indoors at a room temperature of about 20° C. and a relative humidity of 50-60% 10-15 days before the start of floral branch hydroponics; prepare 10-50 mg/L of gibberellin solution and spray it to the leaf buds on the upper part of the seedling stem every 5-7 days to promote the buds to germinate as soon as possible, and stop spraying after the leaves are unfolded. watering with flowerpots, the nutrient solution is poured on the poplar rootstock growth substrate in the pot, and the nutrient solution is composed of 0.02-0.05% of borax, 0.1-0.2% of superphosphate and 0.05-0.1% of compound urea aqueous solution. The combination of the two technical measures can increase the nutrient supply of potted seedlings from the root to the top, ensuring that sufficient nutrients are quickly provided for the floral branches after grafting.

Step 5, hydroponic management of female floral branches: after the leaf buds of the potted poplar seedlings start to germinate for 2-3 days, the hydroponics of male floral branches is started. After 5-7 days of hydroponics of the male floral branches, the female floral branches are then placed in a room with a room temperature of about 20° C. and a relative humidity of 50-60% for hydroponics. The container used for the hydroponics of female floral branches is suitable to choose plastic products with a diameter of 25-35 cm and a depth of 40-50 cm. A circular water outlet with a diameter of 1.5-2 cm is opened 0.3-0.5 cm away from the bottom of one side of the plastic container, which is equipped with a cylindrical rubber plug with the same diameter at the bottom and a slightly larger diameter at the other end. The length of the rubber plug is 3-5 cm to facilitate the operation of changing the water in the container without moving the floral branches, thereby reducing the damage to the roots of the floral branches during hydroponics.

Step 6, grafting of female floral branches and nutrient-supply seedlings, i.e. rootstocks: place the female floral branches in a room with a room temperature of about 20° C. and a relative humidity of 50-60% for hydroponics. The floral branches are grafted with potted poplar seedlings by Marching method. The thickness of poplar seedlings used for grafting should be similar to or slightly thinner than that of female floral branches; 1-3 poplar seedlings are grafted for each female floral branch according to its height; the grafting position should be at the bottom of the flower bud and as close as possible to the flower bud; when grafting more than 2 poplar seedlings, the grafting operation should be carried out in different positions of the female floral branches. The above-mentioned grafting time and grafting position are most conducive to the healing of floral branches and potted seedlings and the absorption of nutrients by flower buds in the comparative experiments.

Step 7, management of female floral branch nutrient-supply seedlings, i.e. rootstocks: after grafting, the potted poplar seedlings will be managed normally, and the potted poplar seedlings will be watered every 5-7 days according to the water status of the potted substrate. When watering, the nutrient solution shall be applied at the same time, and the nutrient solution is composed of 0.02-0.05% of borax, 0.1-0.2% of superphosphate and 0.05-0.1% of compound urea aqueous solution, maintaining the substrate temperature of the rootstock growth at 20-22° C., so as to facilitate the rapid absorption of substrate nutrients by the rootstock roots. The above-mentioned comprehensive technology can ensure that the potted poplars can quickly absorb and transport the substrate nutrients from the rootstocks after grafting, so as to effectively meet the nutrient requirements for the growth and development of flower buds.

Step 8, hydroponics management of female floral branches: the grafted female floral branches will continue to be placed in a hydroponic container for hydroponics. The initial indoor temperature is kept at about 20° C. during the day and no less than 5° C. at night, and the water is changed every 2-3 days. The cuts of the branches are rinsed when changing the water to prevent the mucus secreted from affecting water absorption; if the cuts at the lower end of the branches have changed color or even rotted, trim the cuts in time and clean the hydroponics container. Oxygen is introduced into the hydroponic solution once a day to ensure that there is enough oxygen in the water. When the temperature rises in the later stage, the water is changed every 1-2 days, and the nutrient solution is added when changing the water; the nutrient solution is composed of 0.02-0.05% of borax, 0.1-0.2% of superphosphate and 0.05-0.1% of compound urea aqueous solution; the nutrient solution is sprayed on the back of the leaves of the female floral branches at 9:00, 10:00 and 15:00 every day. Through the above-mentioned various technical measures, the nutrient requirements for the development of flower buds on female floral branches can be further improved.

Step 9, pollen collection and pollination: when there are a small amount of small flowers at the lower end of the male inflorescence, a piece of clean white paper or sulphurous acid paper can be spread under the hydroponic container to let the pollen fall on the paper, and when the entire male inflorescence is all mature and spread pollen, take down the inflorescence and put it in a sieve, and sift out the bracts and other sundries on the inflorescence to prevent mixing in the pollen. Shake the inflorescence gently with hands every day, after 2-3 days, wrap the collected pollen with clean white paper or sulphurous acid paper; place the pollen in a desiccator and store it at a low temperature of about 3-5° C. When the female flower stigma is crystal-clear and secretes sap, pollination can be started. Dip a small amount of pollen with a writing brush and sprinkle it on the stigma. The brush should not touch the stigma during pollination and the amount of pollination should not be too much. Use a magnifying glass to observe the amount of the pollen on the stigma until the stigma is evenly densely covered with pollen. It should be noted that all parts of the same female inflorescence must receive pollen. Due to the inconsistent opening of each florets of the female inflorescence, pollination can be continuously performed for 2-3 days.

Step 10, management of female floral branches after pollination: change the water frequently after pollination, preferably once a day. If tap water is used, the tap water should be placed indoors for 12 h before use. The indoor temperature is controlled at 22-25° C., and the relative humidity is not less than 80% in the initial stage and not less than 50% in the later stage. After pollination, all the leaf buds at the bottom of the branches are removed, and a few top leaf buds are retained. After the leaves unfold, the growth points are removed, and the transpiration pull is retained without excessive consumption of nutrients.

Step 11, harvesting of hybrid seeds: when the capsules start to turn from green to yellow, put them in a small paper bag to prevent the seeds with fluff from flying when the fruit get ripe; after the capsules are all opened, remove the paper bag. Take out the seeds with pointed tweezers and place them separately according to the hybrid combination.

TABLE 1

Comparison of seed setting condition between the method of the invention and the conventional method

| Hybrid combination | Method | Average diameter of floral branches/ cm | Average inflorescence number per flower branch/ piece | Average number of capsules per infructescence/ grain | Average number of seeds per capsule | Total number of seeds/ grain |
| --- | --- | --- | --- | --- | --- | --- |
| Zhongqian 3 × Juba poplar | Original method | 2.4 | 10 | 30 | 45 | 1840 |
| | The method of the invention | 2.5 | 12 | 35 | 43 | 1920 |
| Danhong poplar × Zhonghan 17 | Original method | 2.3 | 12 | 32 | 52 | 1750 |
| | The method of the invention | 2.0 | 11 | 34 | 55 | 1762 |
| 169 × Juba poplar | Original method | 2.8 | 14 | 29 | 55 | 1982 |
| | The method of the invention | 2.5 | 16 | 33 | 51 | 2012 |

Note:
1. In each hybrid combination, the number of floral branches applying the conventional method and the method of the invention is 20 respectively;
2. The number of seeds refers to mature and plump-eared seeds.

It can be seen that compared with the conventional method, the method of the invention can not only realize better seed quality, but also improves the seed-setting rate and can be used in scientific research to efficiently carry out hybridization of poplars.

Although the embodiment of the invention have been shown and described, for the ordinary technicians in the field, it can be understood that various changes, modifications, substitutions can be made to these embodiments without departing from the principle and spirit of the invention, and the scope of the invention is defined by the appended claims and the equivalents.

What is claimed is:

1. A method for improving nutrient supply of female floral branches of *Populus deltoides* artificial hybridization, comprising the following steps:
    step 1, cultivation of female floral branch nutrient-supply seedlings, i.e., floral branch inarching rootstocks
    in March of a year before cross pollination, branches of the same year of a hybrid female parent with a same pedigree number are selected to make cuttings, and then cuttage propagation is performed; after all seedlings have fallen leaves at end of November, a weakly lignified part of an upper part is cut off, keeping a seedling height of 1.5-2.0 m, and then a seedling container is moved from a field to a greenhouse;

or for 1-year-old cuttings that are not easy to obtain female floral branch strain, *Populus deltoides* or *P. euramerican* poplar with a same genetic relationship or close genetic distance with the female branch strain is selected for cuttage or current year seedlings are transplanted in autumn of 1 year before a floral branch is picked, and the transplanting is completed before seedlings fall leaves; after the transplanting, weakly lignified parts of upper parts of the seedlings are truncated, and the number of the transplanted seedlings is 2-3 times the number of hydroponic floral branches, so as to select seedlings with similar thickness of the hydroponic floral branches as rootstocks for grafting;

step 2, management of the female floral branch nutrient-supply seedlings, i.e., the floral branch grafting rootstocks 10-15 days before hydroponics of cross-pollination floral branch, the female floral branch nutrient-supply seedlings are placed in a room with a room temperature of 20° C. and a relative humidity of 50-60%, and gibberellin solution with a concentration of 10-50 mg/L is sprayed on upper parts of the female floral branch nutrient-supply seedlings every 5-7 days until the female floral branch nutrient-supply seedlings are wet, and the spraying is stopped after leaf buds germinate; watering with flowerpots, nutrient solution is poured on poplar rootstock growth substrate in the flowerpots, and the nutrient solution is composed of 0.02-0.05% of borax, 0.1-0.2% of superphosphate and 0.05-0.1% of compound urea aqueous solution;

step 3, hydroponic management of male and female floral branches after the leaf buds of the female floral branch nutrient-supply seedlings start to germinate for 2-3 days, the hydroponics of the male floral branches is started; after 5-7 days of the hydroponics of the male floral branches, the hydroponics of hybrid female floral branches is started, keeping a room temperature at 20° C. and a relative humidity of 50-60% during the hydroponics;

step 4, grafting of the hydroponic female floral branches and nutrient-supply seedlings, i.e., inarching rootstocks the female flower branches are hydroponically cultured indoors at the room temperature of 20° C. and the relative humidity of 50-60%; the female floral branches and the nutrient-supply seedlings are grafted, and the grafting method is an inarching method;

step 5, after the grafting, management of the nutrient supply of the female floral branches, i.e. the inarching rootstocks watering is carried out timely according to moisture status of nutrient-supply seedling substrate every 5-7 days, and the nutrient solution is applied at the same time when the watering; and a substrate temperature for rootstock growth is kept at 20-22° C. to facilitate rapid absorption of substrate nutrients by rootstock roots;

step 6, hydroponic management of the female floral branches after the inarching is completed the grafted female floral branches are then placed in a hydroponic container for hydroponics; an initial indoor temperature is kept at 20° C. during the day and no less than 5° C. at night, and water is changed every 2-3 days;

when the temperature rises in a later stage, the water is changed every 1-2 days, and the nutrient solution is added when changing the water; and the nutrient solution is sprayed on backs of leaves of the female floral branches;

wherein in step 3, a container used for the hydroponics of the female floral branches has a diameter of 25-35 cm and a depth of 40-50 cm, a circular water outlet with a diameter of 1.5-2 cm is opened 0.3-0.5 cm on a side of the container away from a bottom of the container, and the circular water outlet is equipped with a cylindrical rubber plug with a length of 3-5 cm;

wherein in step 6, when changing the water, cuts of the grafted female floral branches are rinsed;

if the cuts at lower ends of the grafted female floral branches have changed color or even rotted, the cuts are trimmed in time and a hydroponics container is cleaned; and oxygen is introduced into hydroponic solution once a day to ensure that there is enough oxygen in the water;

wherein a soil ball is necessary when the transplanting in step 1, and a diameter of the soil ball is smaller than an inner diameter of a container to be transplanted, meanwhile a height of the soil ball is 6-10 cm lower than the container; a bottom and surroundings of the container are filled with turf and soil mixed in a volume ratio of 2:1, and after compaction, roots are irrigated with a mixed solution of 100-150 mg/L of indoleacetic acid and naphthylacetic acid when watering.

2. The method for improving nutrient supply of female floral branches of *Populus deltoides* artificial hybridization according to claim 1, wherein a thickness of poplar seedlings used for grafting in step 4 is similar to or thinner than that of the female floral branches; 1-3 poplar seedlings are grafted for each of the female floral branches according to its height; a grafting position is at a bottom of a flower bud and as close as possible to the flower bud; when grafting more than 2 poplar seedlings, the grafting operation is carried out in different positions of the female floral branches.

* * * * *